(12) United States Patent
Flores et al.

(10) Patent No.: US 8,777,903 B2
(45) Date of Patent: Jul. 15, 2014

(54) CATHETER PATCH APPLICATOR ASSEMBLY

(75) Inventors: Jesus Flores, El Paso, TX (US); Scott Tufts, El Paso, TX (US)

(73) Assignee: CareFusion 2200, Inc., San Diego, CA (US)

( * ) Notice: Subject to any disclaimer, the term of this patent is extended or adjusted under 35 U.S.C. 154(b) by 434 days.

(21) Appl. No.: 12/910,400

(22) Filed: Oct. 22, 2010

(65) Prior Publication Data

US 2012/0101443 A1    Apr. 26, 2012

(51) Int. Cl.
*A61M 5/32* (2006.01)
(52) U.S. Cl.
USPC ........................................ 604/174; 604/506
(58) Field of Classification Search
USPC ............... 604/174–180, 288.01–288.04, 604/304–308, 500, 506–508, 513
See application file for complete search history.

(56) References Cited

U.S. PATENT DOCUMENTS

| | | | |
|---|---|---|---|
| 5,569,207 A | 10/1996 | Gisselberg et al. | |
| 5,631,322 A | 5/1997 | Veronese et al. | |
| 6,447,798 B1 | 9/2002 | Munro et al. | |
| 6,572,588 B1 * | 6/2003 | Bierman et al. | 604/180 |
| 6,663,604 B1 * | 12/2003 | Huet | 604/263 |
| 6,683,120 B2 | 1/2004 | Munro | |
| 6,969,372 B1 * | 11/2005 | Halseth | 604/164.08 |
| 2006/0161109 A1 * | 7/2006 | Huet | 604/174 |
| 2012/0109036 A1 * | 5/2012 | Sambasivam et al. | 602/54 |
| 2012/0150123 A1 * | 6/2012 | Lawrence et al. | 604/180 |

OTHER PUBLICATIONS

"at" definition. Merriam-Webster Online Dictionary. <http://www.merriam-webster.com/dictionary/at>.*
"toward" definition. Merriam-Webster Online Dictionary. <http://www.merriam-webster.com/dictionary/toward>.*

* cited by examiner

*Primary Examiner* — Kami A Bosworth
(74) *Attorney, Agent, or Firm* — Arent Fox LLP

(57) ABSTRACT

In accordance with aspects of the present invention, an applicator assembly suitable for application of a catheter patch about an insertion site of a percutaneous device includes a body having a distal end, a proximal end, and laterally extending right and left side gripping members, a pull tab member attached toward the proximal end of the body, and a release tab connected to the pull tab member, wherein the release tab is positioned toward the distal end of the body so that a lower surface of the release tab abuts an upper surface of the body. The release tab may have a securing mechanism for securing a catheter patch to a lower surface of the body toward the distal end of the body. A method of applying a catheter patch about an insertion site of a percutaneous device using an applicator assembly is provided.

30 Claims, 7 Drawing Sheets

CATHETER PATCH APPLICATOR ASSEMBLY

BACKGROUND

1. Field

The present disclosure relates to a catheter patch applicator assembly and method of use thereof, and more particularly, to a catheter patch and applicator assembly that permits single-hand sterile application of a catheter patch to a patient's skin for lubricating catheters, as surgical dressings, and/or as wound dressings while keeping fingers away from the insertion site and the patient's skin.

2. Description of Related Art

Surgical dressings, wound dressings, and catheter-securing patches for use with catheters or other percutaneous devices, such as feeding tubes, orthopedic fixation pins, or electrical leads, for example, are common in the prior art. The primary concern with transdermal access into the body is the prevention of infection and irritation to the insertion site of the percutaneous device.

For example, long-term care and vascular access catheters are increasingly used to provide indefinite access to a patient's blood vessels for drawing blood or administering medication. The placement of a catheter often relieves a patient of having to endure multiple sticks of a needle once an intravenous (IV) site is established and preserves the integrity of blood vessels, for example, by providing a single site for prolonged access to the patient's circulatory system. The significant increase in the use of long-term catheterization of patients, including in a wide array of settings, such as hospitals, nursing homes, and home health care, for example, creates even greater need for the prevention of irritation to the skin and microbial intrusion into the insertion site.

Each time a dressing is applied to stabilize or protect the insertion site, there exists an opportunity for foreign contamination of the insertion site via the fingers and hands of a technician or medical provider, for example. Long-term applications require repeated changing of the dressing around the percutaneous puncture site. Each time the dressing is changed, an opportunity arises for bacteria or some other foreign contaminant to infect or otherwise irritate the puncture or wound site.

Medical practitioners are trained persistently on the methods of sterile application of a dressing in order to lower the risk of infection or contamination to a percutaneous insertion site. Unfortunately, the manner in which dressings or patches of the related art are designed and/or applied often requires the use of both hands to hold and apply a dressing to a catheter site, or the placement of fingers near the insertion site to hold and/or apply the dressing or patch. This significantly increases the likelihood of contamination of a sterilized IV site or the sterilized patch itself by the hands and/or fingers.

There exists a need in the field for a catheter patch applicator that permits the efficient application of the patch around percutaneous devices of varied sizes while helping keep the hands and/or fingers from contacting the catheter patch and/or away from the insertion site and the patient's skin.

SUMMARY

In accordance with aspects of the present invention, an applicator assembly suitable for application of a catheter patch about an insertion site of a percutaneous device includes a body having a distal end, a proximal end, and laterally extending right and left side gripping members, a pull tab member attached toward the proximal end of the body, and a release tab connected to the pull tab member, wherein the release tab is positioned toward the distal end of the body so that a lower surface of the release tab abuts an upper surface of the body.

In accordance with another aspect of the present invention, the release tab may have a securing mechanism for securing a catheter patch to a lower surface of the body toward the distal end of the body.

In accordance with yet another aspect of the present invention, the pull tab member may include a notch and a step for placement of a finger in the notch to apply a force against the step in a direction toward the proximal end of the body to disengage the catheter patch from the release tab.

In accordance with yet another aspect of the present invention, a method of applying a catheter patch about an insertion site of a percutaneous device may include providing an applicator assembly having a body with a distal end, a proximal end, and laterally extending right and left side gripping members, a pull tab member attached toward the proximal end of the body, and a release tab connected to the pull tab member, wherein the release tab is positioned toward the distal end of the body so that a lower surface of the release tab abuts an upper surface of the body, and wherein a catheter patch comprising a tacky layer is secured to the applicator assembly, exposing a lower surface of the tacky layer of the catheter patch, applying pressure along peripheral edges of the right and left side gripping members to create an access channel suitable for accessing an aperture formed in the tacky layer, positioning the percutaneous device within the aperture formed in the tacky layer via the access channel, contacting the exposed lower surface of the tacky layer with the skin adjacent the percutaneous device insertion site, applying pressure to the applicator assembly to hold the tacky layer against the skin, applying pressure to the pull tab member in a direction toward the proximal end of the body to displace the release tab away from the distal portion of the body and disengage the tacky layer from the release tab, and raising the applicator assembly away from the percutaneous site to disengage the applicator assembly from the catheter patch.

It will become readily apparent to those skilled in the art from the following detailed description, wherein it is shown and described only exemplary configurations of a catheter patch applicator assembly. As will be realized, the invention includes other and different aspects of a catheter patch and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
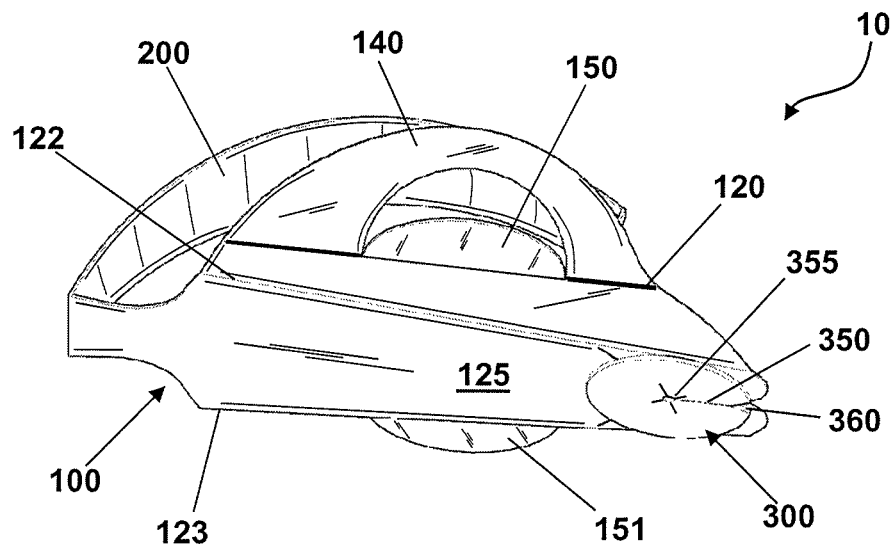
FIG. 1 is a bottom right perspective view of a catheter patch applicator assembly, in accordance with certain aspects of the present invention.
Figure 2:
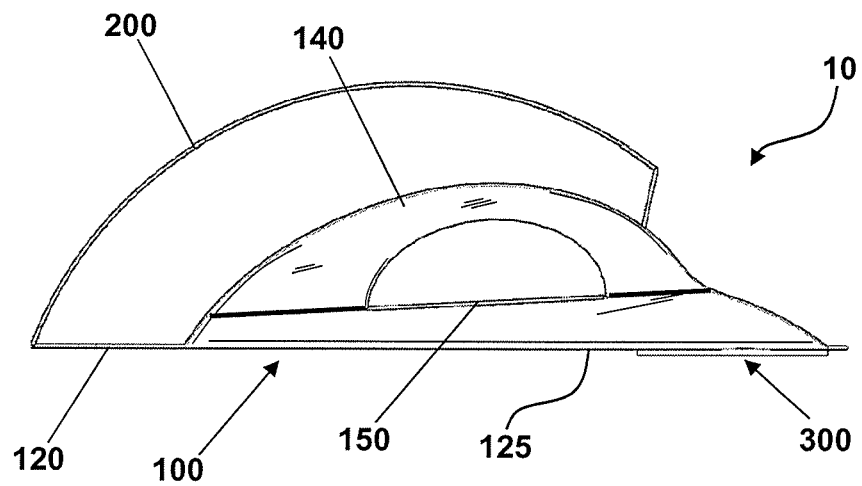
FIG. 2 is a right side view of the catheter patch applicator assembly of FIG. 1, in accordance with certain aspects of the present invention.

Various aspects of a catheter patch applicator assembly may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of a catheter patch and applicator assembly in addition to the orientation depicted in the drawings. By way of example, if a catheter patch and applicator assembly in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of a catheter patch and applicator assembly may be illustrated with reference to one or more exemplary embodiments. As used herein, the term "exemplary" means "serving as an example, instance, or illustration," and should not necessarily be construed as preferred or advantageous over other embodiments of a catheter patch and applicator assembly disclosed herein.

The catheter patch applicator assembly may be compact and ergonomically designed. As shown in FIGS. 1-5, a catheter patch and applicator assembly 10 may comprise an applicator assembly 100 and a catheter patch 300 mounted to a frontal portion thereof. The applicator assembly 100 is configured with a main body section 120 and a pull tab member 200, which is preferably integrally formed with the main body section 120 from a thin, flexible plastic material, such as polypropylene or polyvinyl chloride (PVC).

The main body section 120 comprises right and left side gripping members 140 and 141, which extend laterally away from respective right and left longitudinal edges 122 and 123 of a substantially planar lower surface 125. The longitudinal edges 122 and 123 may be formed by creasing or pre-bending the flexible plastic, for example, so that the right and left side gripping members 140 and 141 extend up and away at an angle from the planar lower surface 125, allowing a user to more easily grasp the applicator assembly 100 with one hand in a comfortable position for application of the catheter patch 300 around a percutaneous insertion site.

Right and left side shield tabs 150 and 151 may be provided, such as by punching a semicircle pattern, for example, into each of the right and left side gripping members 140 and 141. The right and left side shield tabs 150 and 151 may be disposed in an extended position from the gripping members by bending the tabs downward and away from the respective gripping members. In addition to the function of the shield tabs described below, the shield tabs also function as a means of shielding the user's fingers from contact with the patient's skin during use of the applicator assembly.

Figure 6:
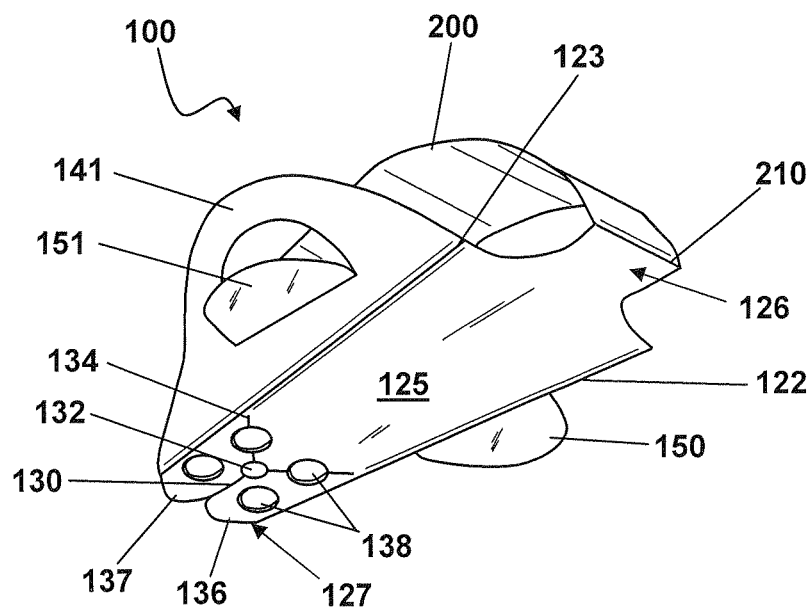
FIG. 6 is a bottom left perspective view of the catheter patch applicator assembly of FIG. 1, in accordance with certain aspects of the present invention.

As illustrated in FIG. 6, the substantially planar lower surface 125 may be configured with a tail section 126 and a nose section 127. The tail section 126 connects to the pull tab member 200 at or toward an optionally narrowed proximal end and may be contoured to sweep out on either side to define a continuous contoured edge with an outer edge of the right and left side gripping members 140 and 141. The right and left side longitudinal edges 122 and 123 may be configured so that the substantially planar lower surface 125 tapers from a wider lateral dimension toward the tail section 126 to a narrower lateral dimension toward the nose section 127. The nose section 127 may include an access channel 130 that extends from a central portion of the nose section 127, optionally including an aperture 132, to a forward peripheral edge of the nose section 127 and divides the nose section into right and left nose tabs 136 and 137. Mounting elements, such as a surface, posts, or preferably apertures 138, may be provided on each of the right and left nose tabs 136 and 137 for coupling a catheter patch 300 to the applicator assembly 100.

As shown in FIGS. 3-6, the pull tab member 200 may be configured to bend forward from the tail section 126 at or toward a hinge point 210, which may be a crease or fold in the plastic material, for example, to connect to a release tab 250. The release tab 250 is fixedly connected to or preferably integrally formed with the pull tab member 200. The release tab 250 may be formed with a securing mechanism, such as a retaining mechanism, posts, or preferably through-holes 252, and a central channel 253. A finger notch 220 may be provided in a forward portion of the pull tab member 200, and the forward portion of the pull tab member may be bent along a fold 222 to provide a lateral step 225 that is ergonomically situated for a user to actuate release of the release tab 250 through an applied force against the step 225.

Figure 7:
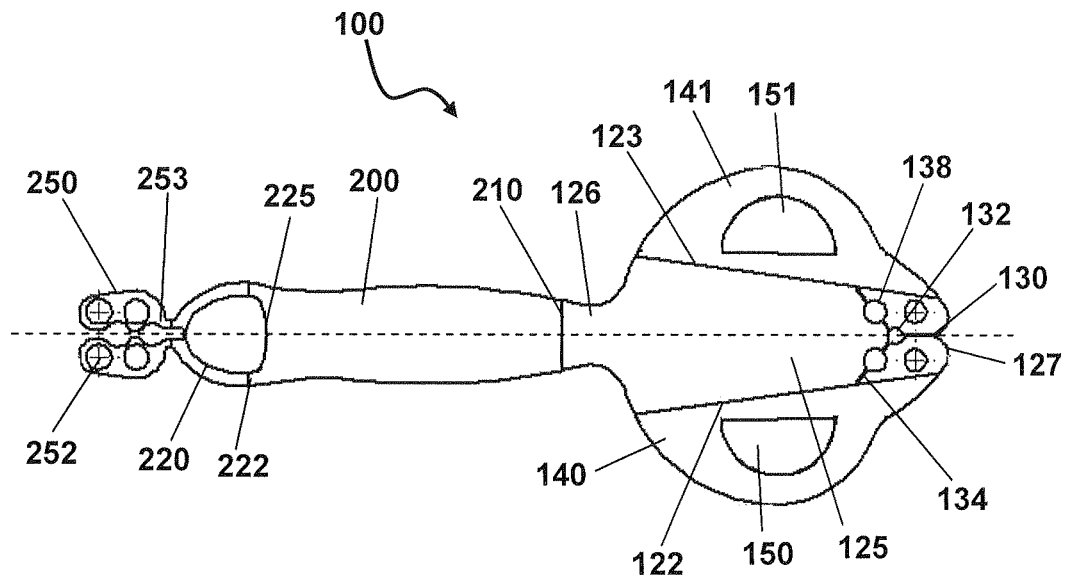
FIG. 7 is a top view of an integrally formed catheter patch applicator assembly, in accordance with certain aspects of the present invention.

As shown in FIG. 7, the applicator assembly 100 may be integrally formed from a single piece of material, preferably stamped from a sheet of thin, flexible plastic material, such as a polypropylene or polyvinyl chloride. The material may be transparent to enhance the user's ability to locate and maintain a line of site with the percutaneous insertion site during application of the catheter patch. During assembly, and with reference to FIGS. 1-6, the release tab 250 may be positioned over the nose section 127 so that the pull tab member 200 is bent in an arcuate manner about hinge point 210. The securing mechanism in the release tab 250 may be aligned with the mounting elements in the nose section 127 with the optional central channel 253 aligned with the optional access channel 130 to permit access of a percutaneous device to the optional aperture 132 through the access channel 130. A lower surface of the release tab 250 may be removably bonded to an upper surface of the nose section 127, for example, to maintain the relative position of the release tab 250 to the applicator assembly 100 during assembly.

Figure 3:
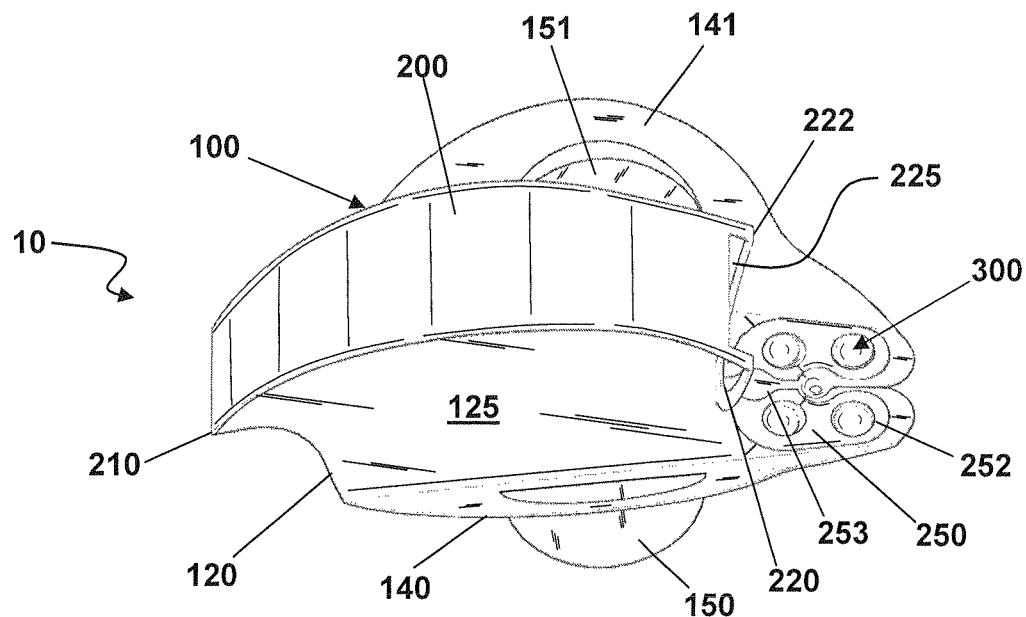
FIG. 3 is a top right perspective view of the catheter patch applicator assembly of FIG. 1, in accordance with certain aspects of the present invention.
Figure 4:
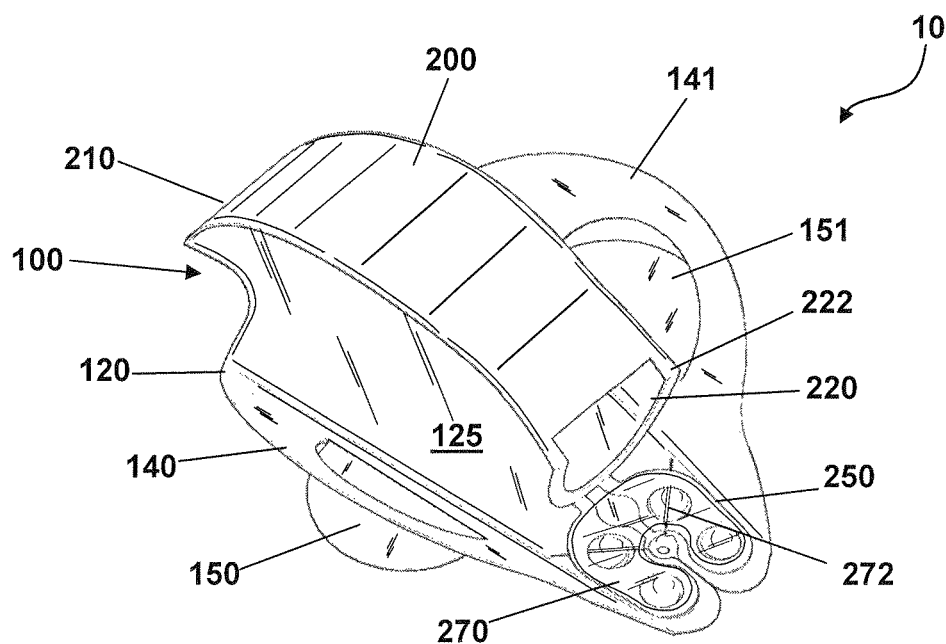
FIG. 4 is a front right perspective view of the catheter patch applicator assembly of FIG. 1, in accordance with certain aspects of the present invention.
Figure 5:
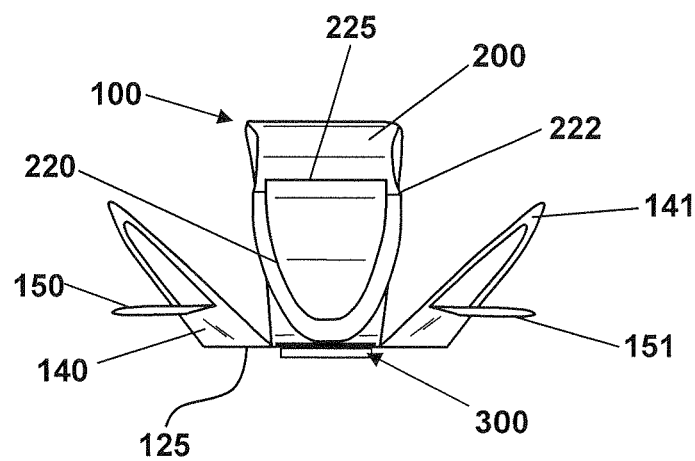
FIG. 5 is a front view of the catheter patch applicator assembly of FIG. 1, in accordance with certain aspects of the present invention.

As shown in FIGS. 1-5 a catheter patch 300 may be formed on or removably abut a lower surface of the nose section 127. The release tab 250 may be formed with a securing mechanism. For example, as shown in FIGS. 3 and 4, the nature and consistency of the catheter patch 300, which may comprise a tacky layer, for example, serves to fill voids between the concentrically aligned through-holes 252 and apertures 138. In this manner, the material that comprises the tacky layer removably couples the catheter patch 300 to the applicator assembly 100 by form fitting through the concentrically aligned through-holes 252 and apertures 138. As shown in FIG. 4, an adhesive layer 270 may be bonded to an upper surface of the release tab 250 to further secure the catheter patch 300 to the applicator assembly 100 by also bonding with portions of the catheter patch 300 bulging through the through-holes 252 and apertures 138. As shown in FIGS. 4 and 6, expansion slits 272 may be provided in the adhesive layer 270 that substantially align with expansion slits 134 that may be provided in the nose section 127, the expansion slits 272 and 134 providing flexibility for release of the catheter patch 300 during application at a percutaneous insertion site.

As mentioned above, the catheter patch 300 may comprise a tacky layer formed of any materials currently in use for catheter patches. Exemplary materials may be found, for example, in U.S. Pat. Nos. 5,569,207, 5,631,322, 6,447,798 and 6,683,120. Preferably, the tacky layer comprises a water soluble polymer, such as a hydrogel. Alternatively or in addition to the aforementioned materials, the tacky layer preferably comprises an antiseptic and/or antimicrobial agent. Suitable antiseptic and/or antimicrobial agents include a chlorhexidine gluconate (CHG) compound, an octenidine compound, an iodine based compound, or other known compounds to increase the effectiveness of the antimicrobial barrier. For example, the catheter patch may include an antiseptic and/or antimicrobial agent on at least a part of a lower surface of the tacky layer to facilitate adherence to the skin when the catheter patch is applied around the insertion site of a patient. The antiseptic and/or antimicrobial agent may be applied to cover a significant portion of the lower surface of the tacky layer of the catheter patch, in particular, substantially the entire patch area surrounding the insertion site.

The lower surface of the catheter patch may be provided with a scrim. The scrim may be composed of any suitable carded non-woven mesh-like material, such as a polypropylene or polyethylene material, for example. The scrim provides additional support to the catheter patch and permits enough of the bottom surface of the catheter patch to contact the skin in order to form an adhesive microbial barrier around the insertion site. During removal of the catheter patch, the scrim may provide structure for lifting the catheter patch away from the skin, enabling a more complete removal of the catheter patch and facilitating an easier cleaning of the area surrounding the insertion site. In addition with another aspect of the present invention, a release liner may be provided on a lower surface of the tacky layer, forming a lower layer of the catheter patch 300. The release liner may be comprised of any material capable of being releasably attached to the tacky layer, such as a 125 micron siliconised polyester material, for example, or any suitable material that will protect the catheter patch during transport and storage, and permit easy release from the tacky layer or an adhesive compound provided on the bottom surface of the tacky layer.

As shown in FIG. 1, an access channel 350 may be provided that extends from an aperture 355 to a peripheral edge of the catheter patch 300. The access channel 350 allows the catheter patch 300, in combination with aspects of the release tab 250 and nose section 127, to be easily positioned around a percutaneous device during application, preferably without disturbing the device to any significant degree. A notch 360, or other suitable guidance feature, may be provided in the catheter patch 300 to further aid in directing the percutaneous device toward the aperture 355 during application.

Another aspect in accordance with the present invention may include providing expansion cross-cut slits that extend in radial directions from the aperture 355. The number, position and radial extension of the individual slits can be varied. The expansion slits allow the catheter patch to easily form fit to a variety of different sized percutaneous devices upon application, ensuring essentially complete coverage and a more effective barrier around the percutaneous device when the catheter patch is applied.

Figure 8:
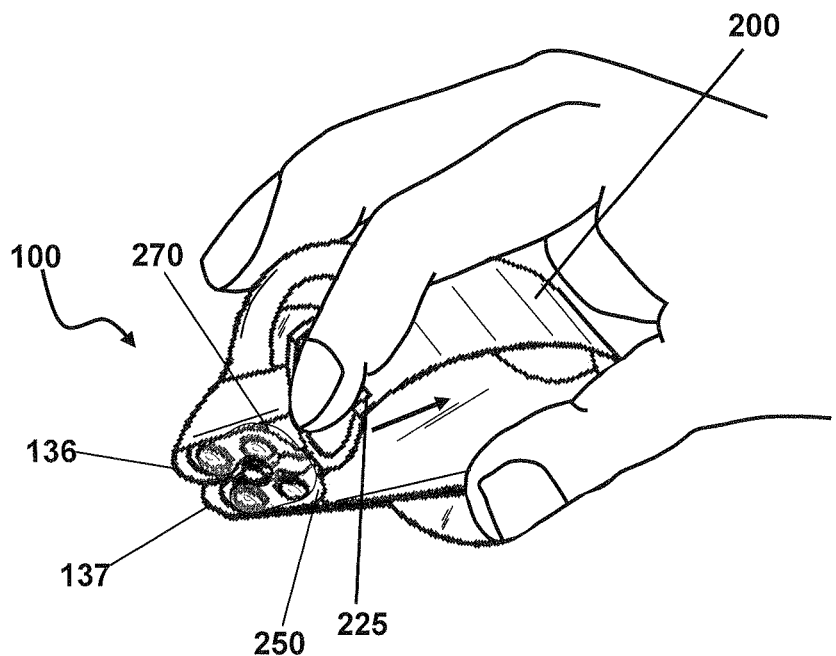
FIG. 8 is a perspective view of the catheter patch applicator assembly of FIG. 1 in a condition of use, in accordance with certain aspects of the present invention.

In use, as shown in FIG. 8, the applicator assembly 100 may be grasped with a thumb and a middle finger, for example, applying a light inward pressure on the right and left side gripping members 140 and 141 so that the nose section 127 is exposed and extended forward of the hand while the tail section 126 is disposed under the palm of the hand. When grasped as such, the pull tab member 200 is arched under at least a portion of the palm, and an index finger, for example, may be positioned to rest against the step 225. With a user holding the applicator assembly 100 with one hand, preferably as described above, a release liner may be disengaged from the catheter patch 300 to expose a lower surface of the tacky layer of the catheter patch. With a lower surface of the frontal portion of the catheter patch 300 exposed, the assembly 100 may be held above the skin and the percutaneous device positioned within the apertures 132, 355 via the channels 130, 253 and 350. Exerting additional inward pressure on the right and left side gripping members 140 and 141 increases a lateral bending of the applicator assembly 100, which results in an outward displacement of each of the right and left nose tabs 136 and 137. The outward displacement of the right and left nose tabs 136 and 137, in turn, causes the access channels 130 and 350 to open from a normally closed position, or further open from a normally slightly open position, allowing easy guidance of the assembly 10 about the percutaneous device.

Once the percutaneous device is positioned within the aperture 355, the exposed lower surface of the tacky layer of the catheter patch may be contacted with the skin, preferably to form an adhesive bond essentially entirely around the insertion site of the percutaneous device. To assist in forming the bond, a slight downward pressure may be applied on an upper surface of the release tab 250. With the catheter patch in position around the percutaneous device, and while continuing to exert a downward pressure on the applicator assembly 100 to hold the catheter patch in position, the index finger may be used to pull the release tab 250 in a proximal direction by applying a rearward pressure against the step 225. The applied pressure forces disengagement of the release tab 250 from that part of the catheter patch secured by the securing mechanism and the adhesive layer 270, if provided. To assist in the process of disengaging the release tab 250 from the catheter patch, the user may, for example, optionally apply pressure to an upper surface of the right and left side shield tabs 150 and 151, respectively, in order to pin the applicator assembly 100 in a stable position against the surface of the skin.

With the release tab 250 disengaged from the catheter patch, the user may release any optional pressure on the right and left side shield tabs 150 and 151 and, while grasping the right and left side gripping members 140 and 141, may raise and safely remove the applicator assembly 100 away from the percutaneous insertion site. In doing so, any remaining portion of the catheter patch secured to or abutting the lower surface of the nose section 127 is also completely disengaged from the applicator assembly 100.

Figure 9:
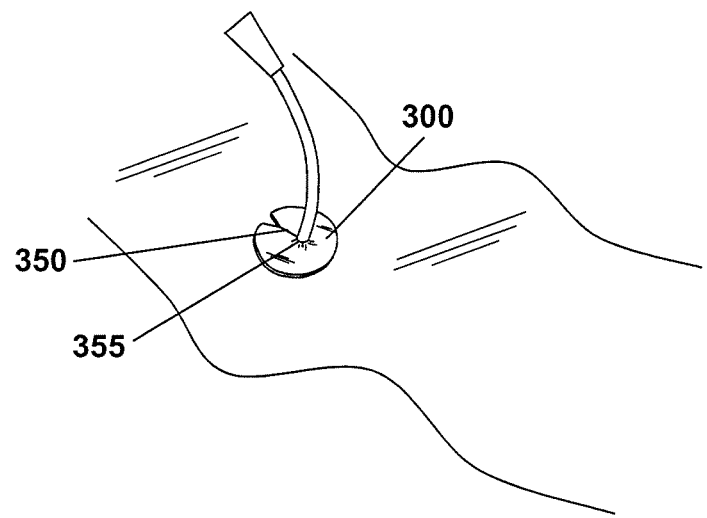
FIG. 9 is a perspective view of a catheter patch as applied to a percutaneous site, in accordance with certain aspects of the present invention.

Application of the catheter patch with one hand enhances the ability of a practitioner to avoid contamination of the insertion site, the catheter patch, and the percutaneous device at or near the insertion site. During application, the fingers and hand of the practitioner are effectively shielded from the insertion site by the applicator assembly 100 and the tacky layer of the catheter patch. As shown in FIG. 9, the aperture 355 preferably form fits to the percutaneous device, allowing the tacky layer of the catheter patch to be easily and effectively applied around various sized catheters or other such percutaneous devices. With the catheter patch thus applied, an effective anti-microbial barrier is created by the catheter patch around the insertion site.

Figure 10:
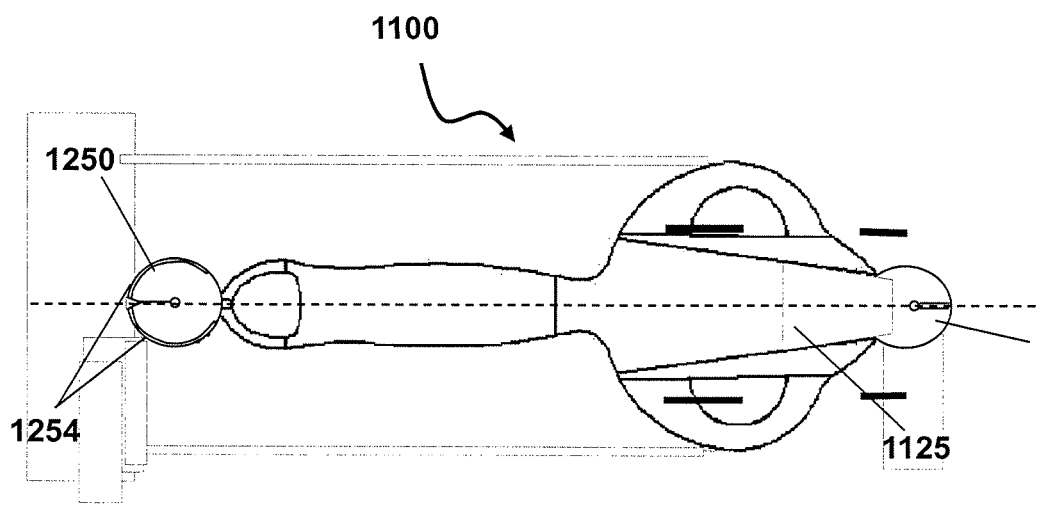
FIG. 10 is a top view of an integrally formed catheter patch applicator assembly, in accordance with certain aspects of the present invention.
Figure 11:
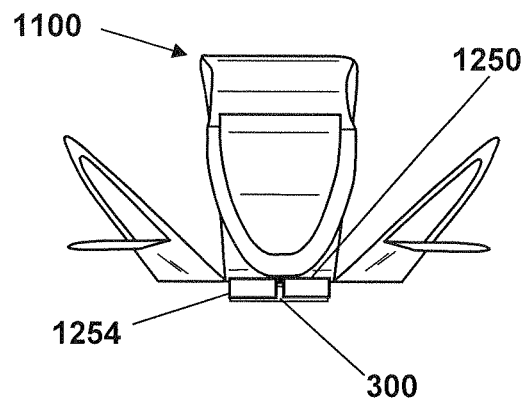
FIG. 11 is a front view of the catheter patch applicator assembly of FIG. 10, in accordance with certain aspects of the present invention.
Figure 12:
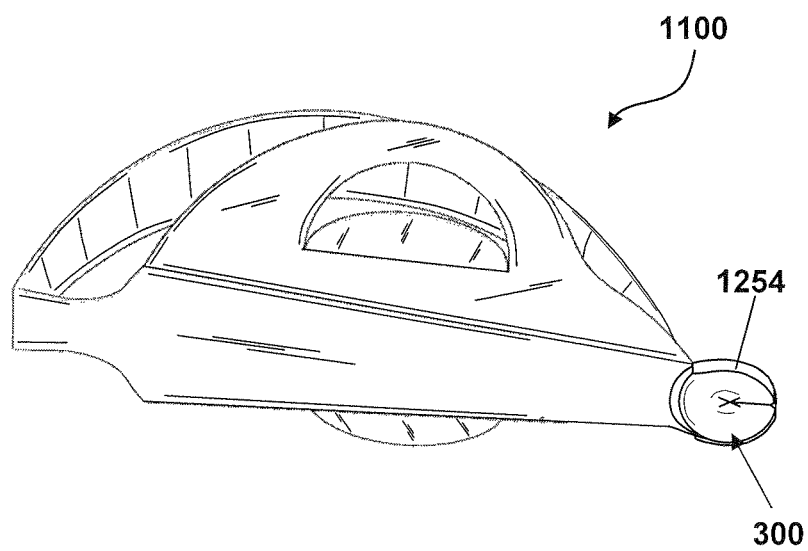
FIG. 12 is a bottom right perspective view of the catheter patch applicator assembly of FIG. 10, in accordance with certain aspects of the present invention.

Although the applicator assembly 100 is described above as having a mounting element that includes apertures 138 on a nose section 127 in cooperation with a securing mechanism that includes through-holes 252 on a release tab 250, a variety of configurations of the nose section 127 and release tab 250 may provide suitable means for securing a catheter patch 300 to, and releasing a catheter patch 300 from, the applicator assembly 100. For example, FIGS. 10-12 illustrate an applicator assembly 1100 in accordance with certain aspects of the present invention that functions in most respects similar to the applicator assembly 100, and, as such, a majority of the structure and functional aspects of the applicator assembly 1100 are not repeated here. The release tab 1250 may be formed with at least one retaining surface 1254, for example, which extends flange-like, preferably orthogonally, from a periphery of the release tab 1250. A radial dimension of the release tab 1250 may be formed to be slightly larger than a radial dimension of a nose section 1127 that extends slightly forward of a substantially planar lower surface 1125. The catheter patch 300 may be formed with a radial dimension equal to or slightly larger than the radial dimension of the release tab 1250. In this manner, and as shown in FIGS. 11-12, when assembled as described above with respect to the applicator 100, the retaining surfaces 1254 of the release tab 1250 may be positioned around the nose section 1127 to effectively cradle the catheter patch 300 and allowing the catheter patch 300 to abut the lower surface of the nose section 1127 until the applicator assembly 1100 is actuated. A bonding material may optionally be used to releasably join an upper surface of the catheter patch 300 to the lower surface of the nose section 1127 until the applicator assembly 1300 is actuated. Actuation of the applicator assembly 1100, as described above with respect to the applicator assembly 100, causes the release tab 1250 to disassociate from the nose section 1127, which, in turn, causes the at least one retaining surface 1254 to slide past the nose section 1127 and disassociate from the catheter patch. With the at least one retaining surface 1254 disengaged from the catheter patch, the user may raise and safely remove the applicator assembly 1100 away from the percutaneous insertion site. In doing so, any portion of the catheter patch remaining attached to the nose section 1127 is also completely disengaged from the applicator assembly 1100.

Figure 13:
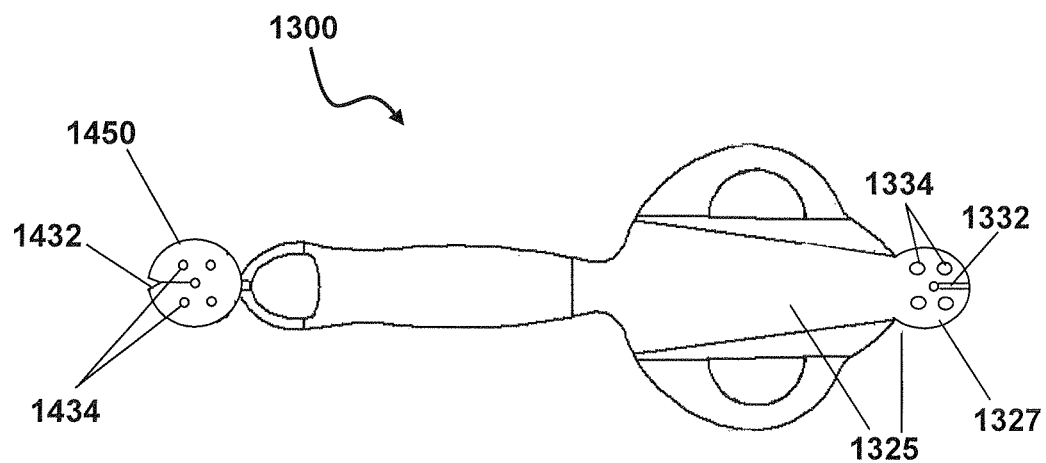
FIG. 13 is a top view of an integrally formed catheter patch applicator assembly, in accordance with certain aspects of the present invention.
Figure 14:
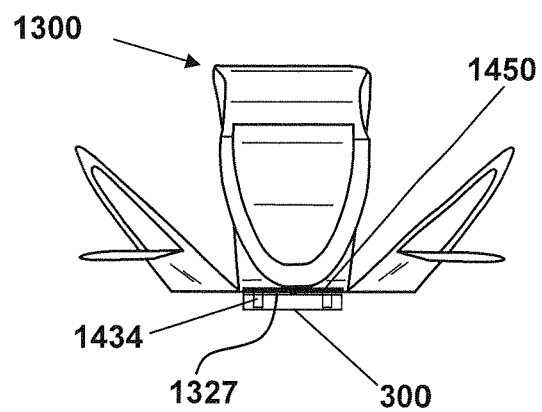
FIG. 14 is a front view of the catheter patch applicator assembly of FIG. 13, in accordance with certain aspects of the present invention.

FIGS. 13-14 illustrate another applicator assembly 1300 in accordance with certain aspects of the present invention. The applicator assembly 1300 functions in most respects similar to the applicator assembly 100, and, as such, a majority of the structure and functional aspects of the applicator assembly 1300 are not repeated here. As shown in FIG. 13, the nose section 1327 of the body may be formed with a positioning notch 1332 and one or more mounting apertures 1334, and the release tab 1450 may be formed with a positioning notch 1432 and one or more retaining posts 1434. In assembling the combination of a catheter patch 300 and an applicator assembly 1300, the applicator assembly 1300 may be prepared for receiving the catheter patch 300 by sliding the retaining posts 1434 through the mounting apertures 1334 so that a lower surface of the release tab 1450 abuts an upper surface of the nose section 1327, the retaining posts 1434 align with and extend through the one or more mounting apertures 1334, and the positioning notches 1432 and 1332 are in substantial alignment. As shown in FIG. 14, a catheter patch 300 may thus abut the lower surface of the nose section 1327 and may be secured to the applicator assembly 1300 by the retaining posts 1434. Actuation of the applicator assembly 1300, as described above with respect to applicator 100, causes the release tab 1450 to disassociate from the nose section 1327, which, in turn, causes the retaining posts 1434 to withdraw from the mounting apertures 1334 and disassociate from the catheter patch. With the retaining posts 1334 disengaged from the catheter patch, the user may raise and safely remove the applicator assembly 1300 away from the percutaneous insertion site, as described previously with respect to the applicator 100. In doing so, any portion of the catheter patch remaining attached to the nose section 1327 is also completely disengaged from the applicator assembly 1300.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly suitable for application of a catheter patch about an insertion site of a percutaneous device, the assembly comprising:
    a body having a distal end, a proximal end, and laterally extending right and left side gripping members;
    a pull tab member attached to the body toward the proximal end of the body; and a release tab directly and fixedly connected to the pull tab member, wherein the release tab is positioned closer to the distal end of the body than to the proximal end of the body so that a lower surface of the release tab abuts an upper surface of the body, wherein the release tab has a securing mechanism for securing a catheter patch to the body.

2. The applicator assembly of claim 1, wherein the catheter patch is securable against a lower surface of the body toward the distal end of the body.

3. The applicator assembly of claim 2, wherein the catheter patch comprises a tacky layer and a release liner releasably attached to a lower surface of the tacky layer.

4. The applicator assembly of claim 3, wherein the tacky layer comprises a polymer gel.

5. The applicator assembly of claim 3, wherein the tacky layer comprises an aperture and an access channel extending from the aperture to an opening at a frontal portion of the catheter patch.

6. The applicator assembly of claim 5, wherein the tacky layer further comprises at least one expansion slit extending from the aperture.

7. The applicator assembly of claim 6, wherein the tacky layer further comprises a notch provided at a periphery of the access channel.

8. The applicator assembly of claim 1, wherein the securing mechanism comprises at least one retaining surface extending substantially orthogonally from the periphery of a lower surface of the release tab.

9. The applicator assembly of claim 1, wherein the body further comprises at least one mounting aperture that cooperates with the securing mechanism to secure the catheter patch to the applicator assembly.

10. The applicator assembly of claim 9, wherein the securing mechanism is at least one through-hole that secures a portion of the catheter patch extending through the at least one mounting aperture.

11. The applicator assembly of claim 10, wherein the at least one through-hole disengages from the catheter patch when an applied force displaces the release tab toward the proximal end of the body.

12. The applicator assembly of claim 10, wherein an adhesive layer is attached to an upper surface of the release tab, and wherein the adhesive layer is releasably bonded to the portion of the catheter patch extending through the at least one through-hole.

13. The applicator assembly of claim 9, wherein the securing mechanism is at least one mounting post provided on the lower surface of the release tab, the at least one mounting post extending through the at least one mounting aperture to secure the catheter patch adjacent to the lower surface of the body toward the distal end of the body.

14. The applicator assembly of claim 1, wherein the pull tab member comprises a notch and a step for placement of a finger in the notch to apply a force against the step in a direction toward the proximal end of the body to disengage the catheter patch from the release tab.

15. The applicator assembly of claim 1, wherein a right side shield tab is provided in the right side gripping member and a left side shield tab is provided in the left side gripping member.

16. The applicator assembly of claim 1, wherein the body, the pull tab member, and the release tab are integrally formed from a common material.

17. The applicator assembly of claim 1, wherein the body further comprises a substantially planar lower surface, a nose section and a tail section, and wherein a lateral dimension of the substantially planar lower surface tapers from a wider dimension toward the tail section to a narrower dimension toward the nose section.

18. The applicator assembly of claim 17, wherein the nose section comprises an access channel and a body aperture, the access channel extending from the body aperture to a forward peripheral edge of the body.

19. The applicator assembly of claim 18, wherein the release tab further comprises a central channel aligned with the access channel to permit access of a percutaneous device to the body aperture.

20. A method of applying a catheter patch about an insertion site of a percutaneous device, the method comprising:
providing an applicator assembly comprising:
a body having a distal end, a proximal end, and laterally extending right and left side gripping members;
a pull tab member attached toward the proximal end of the body; and
a release tab connected to the pull tab member, wherein the release tab is positioned toward the distal end of the body so that a lower surface of the release tab abuts an upper surface of the body;
securing a catheter patch to the applicator assembly, wherein the catheter patch comprises a tacky layer;
exposing a lower surface of the tacky layer;
applying pressure along peripheral edges of the right and left side gripping members to create an access channel suitable for accessing an aperture formed in the tacky layer;
positioning a percutaneous device within the aperture formed in the tacky layer via the access channel;
contacting the exposed lower surface of the tacky layer with skin adjacent percutaneous device insertion site;
applying pressure to the applicator assembly to hold the tacky layer against the skin;
applying pressure to the pull tab member in a direction toward the proximal end of the body to displace the release tab away from the distal portion of the body and disengage the tacky layer from the release tab; and
raising the applicator assembly away from the percutaneous device insertion site to disengage the applicator assembly from the catheter patch.

21. The method of applying a catheter patch of claim 20, wherein the catheter patch is secured adjacent to a lower surface of the body toward a distal portion of the body by a securing mechanism provided on the release tab.

22. The method of applying a catheter patch of claim 21, wherein the securing mechanism comprises at least one retaining surface extending substantially orthogonally from a periphery of the lower surface of the release tab.

23. The method of applying a catheter patch of claim 21, wherein the body further comprises at least one mounting aperture that cooperates with the securing mechanism to secure the catheter patch to the applicator assembly.

24. The method of applying a catheter patch of claim 23, wherein the securing mechanism is at least one through-hole that secures a portion of the catheter patch extending through the at least one mounting aperture.

25. The method of applying a catheter patch of claim 24, wherein an adhesive layer is attached to the release tab and bonded to the portion of the catheter patch extending through the at least one through-hole.

26. The method of applying a catheter patch of claim 23, wherein the securing mechanism is at least one mounting post provided on the lower surface of the release tab, the at least one mounting post extending through the at least one mounting aperture to secure the catheter patch adjacent to the lower surface of the body toward the distal end of the body.

27. The method of applying a catheter patch of claim 20, wherein the pull tab member comprises a notch and a step for placement of a finger in the notch to apply a force against the step in a direction toward the proximal end of the body to disengage the catheter patch from the release tab.

28. The method of applying a catheter patch of claim 20, further comprising a right side shield tab extending from the right side gripping member and a left side shield tab extending from the left side gripping member, wherein the tacky layer is held against the skin by pressure exerted on the left and right side shield tabs.

29. The method of applying a catheter patch of claim 20, wherein the catheter patch further comprises a release liner releasably attached to the lower surface of the tacky layer.

30. The method of applying a catheter patch of claim 20, wherein the tacky layer comprises a polymer gel.

\* \* \* \* \*